(12) United States Patent
Riedel et al.

(10) Patent No.: US 11,394,901 B2
(45) Date of Patent: Jul. 19, 2022

(54) EYE MODEL

(71) Applicant: Alcon Inc., Fribourg (CH)

(72) Inventors: Peter Riedel, Nuremberg (DE); Mario Abraham, Burgthann (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/327,832

(22) Filed: May 24, 2021

(65) Prior Publication Data

US 2021/0281776 A1   Sep. 9, 2021

Related U.S. Application Data

(62) Division of application No. 15/238,451, filed on Aug. 16, 2016, now abandoned.

(30) Foreign Application Priority Data

Nov. 5, 2015 (DE) .......................... 102015014324.7

(51) Int. Cl.
| | | |
|---|---|---|
| *A61B 3/00* | (2006.01) | |
| *H04N 5/33* | (2006.01) | |
| *B26F 1/38* | (2006.01) | |
| *B26D 3/00* | (2006.01) | |
| *G09B 23/30* | (2006.01) | |
| *A61B 3/113* | (2006.01) | |

(52) U.S. Cl.
CPC ............. *H04N 5/33* (2013.01); *A61B 3/0025* (2013.01); *A61B 3/113* (2013.01); *B26D 3/006* (2013.01); *B26F 1/3846* (2013.01); *G09B 23/30* (2013.01)

(58) Field of Classification Search
CPC .. A61F 2/14; A61F 2/141; A61F 2/142; A61F 2/145; A61F 2/147; G09B 23/30; G09B 23/306; G09B 23/23; G09B 23/34; G09B 23/36
See application file for complete search history.

(56) References Cited

U.S. PATENT DOCUMENTS

| | | |
|---|---|---|
| 2,593,150 A | 4/1952 | Jardon |
| 2,673,984 A | 4/1954 | Clarke |
| 3,846,199 A | 11/1974 | Cappelli |
| 4,601,673 A | 7/1986 | Nasca |
| 6,485,142 B1 | 11/2002 | Sheehy |
| 10,400,950 B1 | 9/2019 | Hauser |
| 2009/0004637 A1 | 1/2009 | Carda |
| 2013/0030524 A1 | 1/2013 | Akura |

(Continued)

FOREIGN PATENT DOCUMENTS

| | | |
|---|---|---|
| CN | 201638451 U | 11/2010 |
| CN | 101939774 A | 1/2011 |
| CN | 104091506 A | 10/2014 |

(Continued)

OTHER PUBLICATIONS amazon.com; EISCO Human Eye Model: Website: https://www.amazon.com/EISCO-Human-Model-Parts-Enlarged/dp/B00ARJOSQG, EAN 0849230000479, 0696748231846.

(Continued)

*Primary Examiner* — Robert J Utama

(57) ABSTRACT

An eye model comprises a sclera simulation which is made of a bright plastic material and a pattern which contrasts in color with the sclera simulation, the pattern simulating an eye pupil and/or an iris structure. The eye model is used to calibrate an eye tracking system.

8 Claims, 4 Drawing Sheets

(56) References Cited

U.S. PATENT DOCUMENTS

2013/0317609 A1 11/2013 Green
2014/0170623 A1 6/2014 Jarstad

FOREIGN PATENT DOCUMENTS

| CN | 203898265 U | 10/2014 |
|----|-------------|---------|
| WO | 9014056 A1 | 11/1990 |
| WO | 2005047938 A2 | 5/2005 |

OTHER PUBLICATIONS

Taylor; "Determining the Accuracy of an Eye Tracking System for Laser Refractive Surgery"; Journal of Refractive Surgery; vol. 16; Sep./Oct. 2000; p. S643-S646.

EYE MODEL

TECHNICAL FIELD

The present disclosure relates in general to an eye model. The present disclosure relates in particular to an eye model which is recordable by means of an infrared camera, a method for producing the eye model, and a device for using the eye model in conjunction with an infrared camera.

BACKGROUND

In a number of measurement methods for measuring the eye, electromagnetic radiation (hereinafter "light" for short) is radiated onto and/or into the eye to be examined, and the radiation reflected from the eye is detected and evaluated. Thus, for example, in the field of refractive laser treatment of the human eye, eye tracking systems (so-called eye trackers) having at least one infrared camera are used for recording infrared light reflected from the eye and determining a position and an orientation of the eye based on the recorded infrared images. By use of suitable processing software, a movement of the eye in the course of treatment may thus be detected and quantified.

The determination of the position and the orientation of the eye by means of the eye tracker is based on the detection of eye structures, such as the eye pupil, the iris structure, the limbus, and blood vessels within the sclera, within the recorded infrared images or VIS images. Test objects for use in test measurements (during calibration, for example) of the eye tracker therefore also have such eye structures. The test objects are customarily present as sheet- or plate-shaped objects having an imprinted replica of one or more of the eye structures (for example, only the eye pupil).

For example, a lateral translation of an eye may be simulated and tracked by means of the eye tracker by effecting a two-dimensional relative movement between the eye tracker and the test object. However, it should be noted that the eye (for example, during the refractive laser treatment) may also undergo translations along the optical axis of the eye, and rotations about the optical axis and also about spatial axes extending perpendicularly thereto. Eye trackers nowadays are configured for detecting the described movements. However, within the scope of test measurements it is not possible to adequately simulate all degrees of freedom of the eye movement by means of the sheet- or plate-shaped test objects.

SUMMARY OF EXEMPLARY EMBODIMENTS

An object of the present invention is to provide an eye model for use as a test object within the scope of a test measurement of an eye tracking system.

One aspect of the present invention is an eye model comprising a sclera simulation which is made of a bright plastic material, the plastic material containing polyvinyl chloride at least as the main component, and comprising a pattern which contrasts in color with the sclera simulation, the pattern simulating an eye pupil and/or an iris structure.

As the result of using polyvinyl chloride at least as the main component of the plastic material, no significant diffuse reflection occurs in the sclera simulation during an infrared illumination of the eye model. In one preferable embodiment, the plastic material consists of a polyvinyl chloride.

The sclera simulation made of the plastic material appears bright under infrared illumination. Thus, the pattern contrasts in color with the sclera simulation, even under diffused or direct infrared illumination. The plastic material is preferably white in the area of the sclera simulation.

In one embodiment, the eye model is formed from an eye body whose surface in the area of the sclera simulation forms an annular surface in accordance with the shape of a spherical or ellipsoidal surface. Due to the three-dimensional design of the eye body, in particular due to the convex curvature of the annular surface (which, for example, models a scleral surface of a human eye), by rotating the eye model it is possible to simulate a rotational movement about the optical axis of the eye (z-axis) and about spatial axes extending perpendicularly thereto (so-called eye roll about the x-axis and the y-axis).

The eye body of the eye model may have a flattened area on which at least a portion of the pattern, preferably the complete pattern, is situated. It may be provided that the pattern is situated on only a partial region of the flattened area. At least in this case, the pattern may simulate only the eye pupil, for example, which is preferably centrally situated on the flattened area. In addition, it may be provided that the pattern is situated essentially on the entire region of the flattened area.

The transition from the annular surface to the flattened area may be formed by a ring-shaped edge. The pattern preferably adjoins the ring-shaped edge. The pattern may simulate at least the iris structure, and its outer edge may adjoin the ring-shaped edge. In any case, the pattern may be formed by imprinting or painting of the eye body, or by adhering to the eye body an adhesive element which bears the pattern.

In one embodiment of the eye model, the eye body has a threaded hole on the annular surface or on the side of the annular surface opposite from the pattern. A cross section of the threaded hole may be oriented substantially parallel or substantially rectangular to the flattened area in which at least a portion of the pattern is situated. Preferably, the eye body has a flattened area on the side of the annular surface opposite from the pattern, and is provided with the threaded hole in the region of this flattened area. The threaded hole may be provided for purposes of fastening the eye model.

A further aspect of the present invention is an eye model, in particular the eye model described herein. The eye model includes an eye body having a flattened area, and a bright, in particular white, sclera simulation which surrounds the flattened area in a ring-like manner, wherein a pattern is formed on the flattened area, the pattern contrasting in color with the sclera simulation and simulating an eye pupil and/or an iris structure. The surface of the eye body in the area of the sclera simulation forms a convexly curved annular surface.

A further aspect of the present invention is a method for producing an eye model, in particular for producing one of the eye models described herein. The method comprises provisioning of a plate-shaped or rectangular blank, the blank being made of a bright, in particular white, plastic material which contains polyvinyl chloride at least as the main component, wherein the blank has two oppositely situated blank flat sides. The method also includes cutting or chipping machining of the blank in order to separate at least one eye body from the blank, the separated eye body having a first flattened area which is formed from a first of the blank flat sides, and having a convexly curved peripheral surface which surrounds the first flattened area in a ring-like manner, and forming of a pattern, which contrasts in color with the plastic material and which simulates an eye pupil and/or an iris structure, in an area of the first blank flat side which corresponds to the first flattened area.

It may be provided to separate a single eye body or a plurality of eye bodies from the blank. Separating the plurality of eye bodies may take place, for example, essentially simultaneously, or essentially simultaneously within a portion of the plurality of eye bodies, or chronologically in succession.

Forming the pattern on the first blank flat side may take place after the eye body has been separated from the blank. However, the pattern is preferably formed on the first blank flat side prior to the step of separating the eye body from the blank. In particular the production of a plurality of eye models based on a single blank may be simplified and speeded up in this way.

According to a further development of the method, a threaded hole is introduced into the blank on the second of the blank flat sides, in association with each eye body to be separated from the blank, before the respective eye body is separated from the blank. The separated eye body may have a second flattened area which may be formed by the second blank flat side, and in which the threaded hole may be situated.

A further aspect of the present invention relates to the use of an eye model, in particular the use of one of the eye models described herein, for recording images of the eye model by means of a camera. An infrared camera is used as the camera, and for the eye model, an eye body is used which has a sclera simulation which is made of a bright plastic material containing polyvinyl chloride at least as the main component, and which has a pattern, the pattern contrasting in color with the sclera simulation and simulating an eye pupil and/or an iris structure. It may be provided that the images of the eye model contain at least the pattern and a portion of the sclera simulation.

The infrared camera may be part of an eye tracking system, wherein the eye model is moved relative to the infrared camera while the images are recorded, and the eye tracking system detects eye movements on the basis of the recorded images. For this purpose, it may be provided that the eye tracking system also has a processing unit which is configured for determining a position and/or an orientation of the pattern included by the eye model within the recorded infrared image.

It may also be provided that for use, the eye model is situated on a patient table in the area of a head support of the patient table while the images are recorded. For example, a positioning device for the eye model to which the eye model is fastened (screwed, for example) may be integratable into the head support.

BRIEF DESCRIPTION OF THE DRAWINGS

Supplemental features, advantages, and components of the present invention are apparent from the following description of the appended drawings, which show the following.

DETAILED DESCRIPTION OF THE EXEMPLARY EMBODIMENTS

Figure 1A:
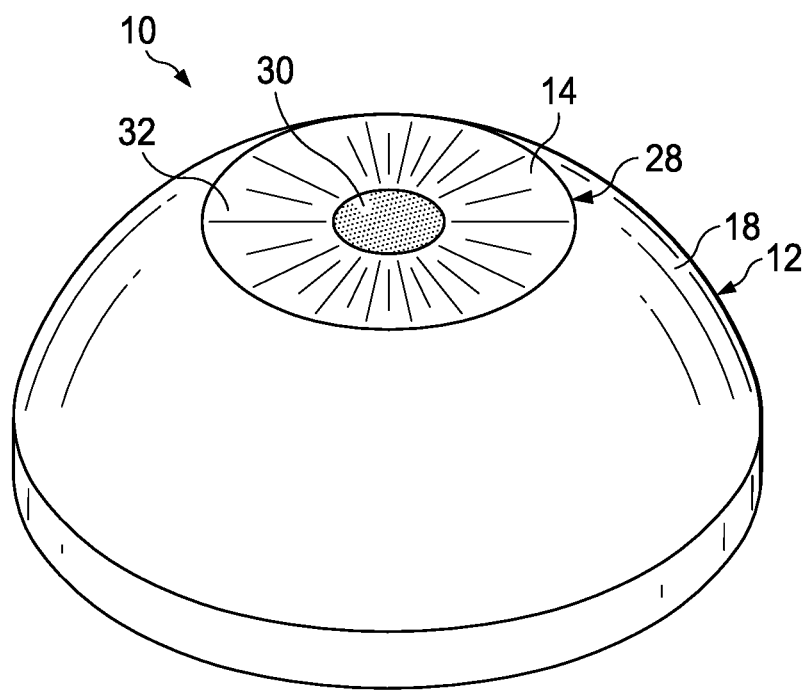
FIGS. 1A to 1D show one exemplary embodiment of an eye model.
Figure 1B:
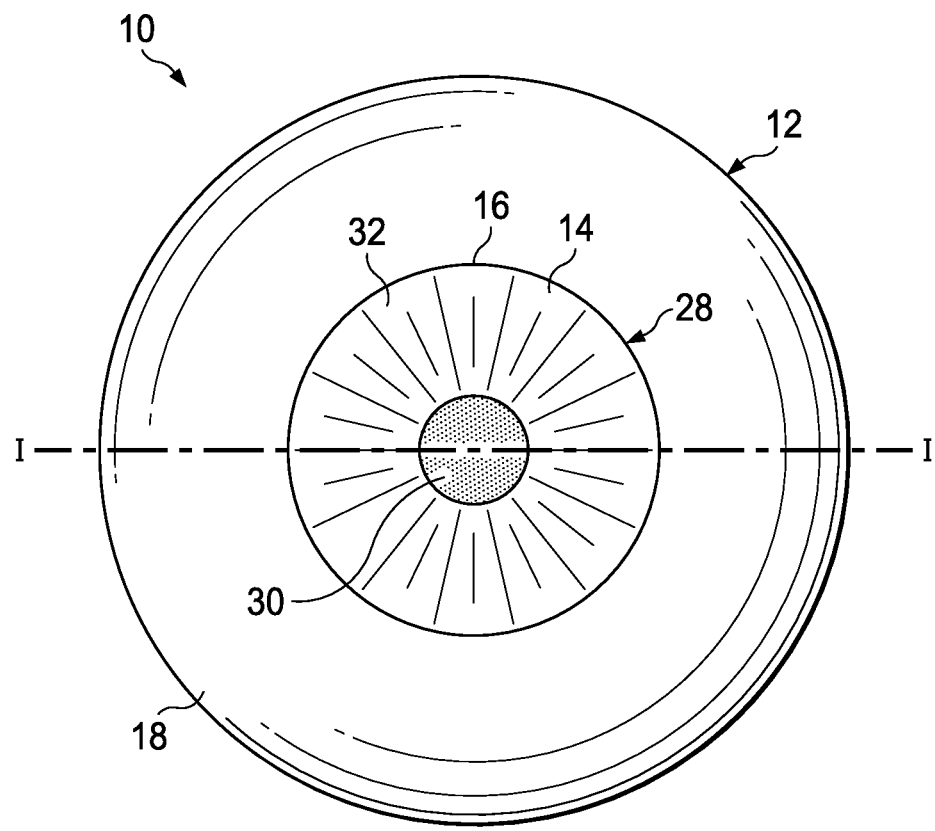
Figure 1C:
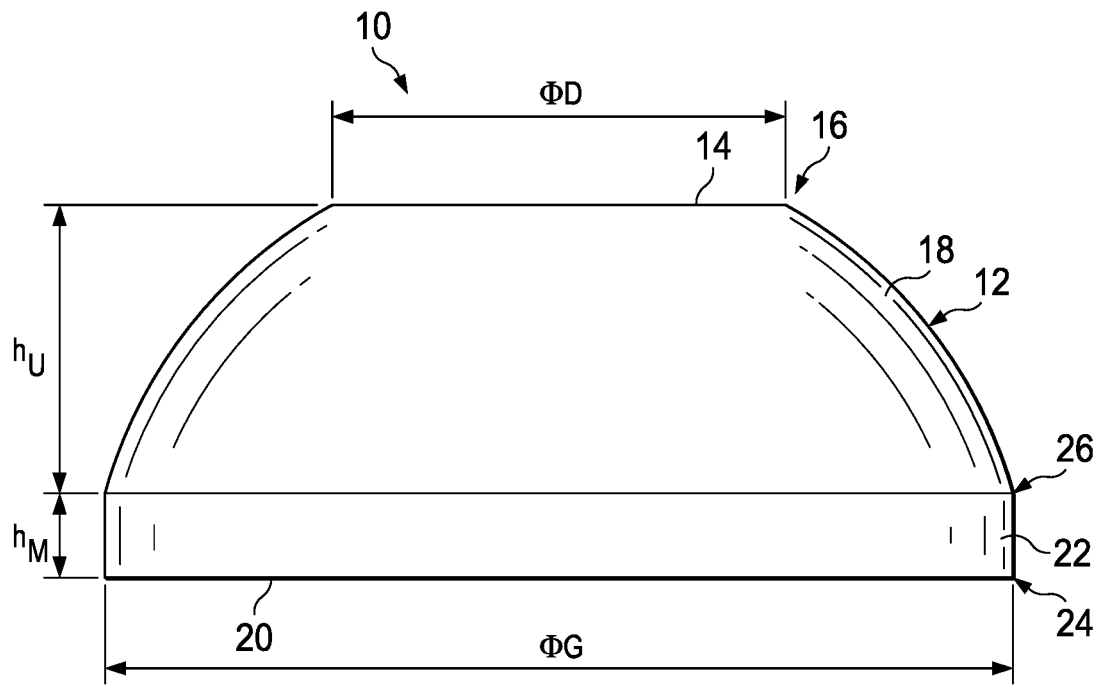
Figure 1D:
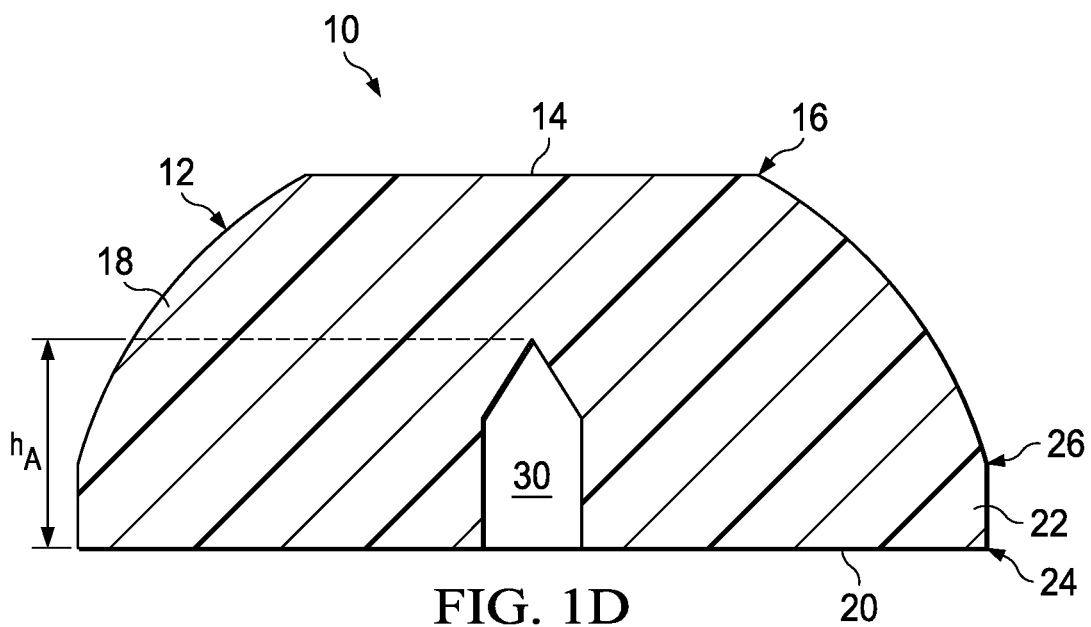

FIGS. 1A to 1D show schematic illustrations of one exemplary embodiment of an eye model, denoted in general by reference numeral 10. FIG. 1A shows a perspective view, FIG. 1B shows a top view, FIG. 1C shows a side view, and FIG. 1D shows a sectional view of the eye model 10 along a section line I indicated in FIG. 1B.

In the exemplary embodiment shown in FIGS. 1A to 1D, the eye model 10 is formed from an eye body 12. The eye body 12 has a first flattened area 14 within which the surface of the eye body 12 is planar. The first flattened area 14 forms a disk-shaped (for example, ellipsoidal and in particular circular) cover surface of the eye model 10. A convexly curved peripheral surface 18 which circumferentially surrounds the cover surface 14 in a ring-like manner is joined to the cover surface 14 via a first ring-shaped edge 16. The peripheral surface 18 is designed as an annular surface which is in accordance with (or which conforms to) the shape of an ellipsoidal surface (for example, a spherical surface).

The eye body 12 also has a second flattened area 20 opposite from the cover surface 14. The second flattened area 20 forms a disk-shaped (for example, ellipsoidal and in particular circular) base area of the eye model 10. It may be provided that the base area 20 (via a ring-shaped edge) adjoins the annular surface 18. In the exemplary embodiment shown in FIGS. 1A to 1D, however, the eye body 12 has a lateral surface 22 which extends between the annular surface 18 and the base area 20. The planar lateral surface 22 describes the shape of a cylindrical surface which adjoins the base area 20 and the annular surface 18, respectively, via two circular edges 24, 26 having the same circumference. In another exemplary embodiment, the lateral surface 22 may have a design which conforms to a conical surface, for example.

The eye model 10 shown in FIGS. 1A to 1D includes a simulation (i.e., replica) of a human sclera. The sclera simulation is formed by the eye body 12, in particular the portion of the eye body 12 that is bordered by the annular surface 18. The eye body 12 is made of white polyvinyl chloride. No significant diffuse reflection takes place within the polyvinyl chloride when the eye body 12 is illuminated with infrared light. The eye body 12 thus appears white, even under infrared illumination.

In another exemplary embodiment, it may be provided that instead of being made of white polyvinyl chloride, the eye body 12 is made of a bright, in particular white, plastic material containing (for example, white) polyvinyl chloride at least as the main component. The plastic material may include further components, such as plasticizers or additional plastics. In any case, the plastic material should be designed in such a way that it appears bright, in particular white, even under infrared illumination.

For the eye model 10 shown in FIGS. 1A to 1D, the simulation includes only a portion of the human sclera. The portion of the eye body 12 having the sclera simulation forms the shape of an ellipsoidal layer (for example, a spherical layer). Alternatively, it may be provided to enlarge the simulated portion of the sclera to form a simulation of essentially the entire sclera. In the latter case, the eye body 12 may assume the shape of an ellipsoidal dome (for example, a spherical dome).

As is apparent in FIGS. 1A and 1B, a pattern 28 is applied to the cover surface 14 of the eye model 10. The pattern 28 includes the simulation of an eye pupil 30 and of an iris structure 32. The pattern 28 extends over the entire flattened area of the eye body 12 which forms the cover surface 14 of the eye model 10. In another exemplary embodiment, it may be provided that the pattern 28 simulates only the iris structure 32 or only the eye pupil 30. At least in this case, it is possible to apply no pattern 28 to an area of the cover surface 14 of the eye model 10 (for example, in the case of only a pupil replica, in an area around the eye pupil 30).

It may also be provided that a portion of the pattern 28 (for example, the simulation of the iris structure 32) extends in a convexly curved surface area of the eye body 12 or is applied entirely in a convexly curved surface area of the eye body 12 (for example, conforming to the shape of the annular surface 18). In the latter case, it may be provided that only the simulation replica of the eye pupil 30 is situated on the cover surface 14 of the eye model 10.

As is apparent in FIGS. 1A and 1B, the simulation of the eye pupil 30 and the simulation of the iris structure 32 contrast in color with the sclera simulation. The simulation of the eye pupil 30 and of the iris structure 32 may be implemented in gray tones, in colors of the RGB color space, or in colors of the CMYK color space.

At least in the exemplary embodiment shown in FIGS. 1B and 1C, the flattened area of the eye body 12 having the pattern 28 is designed as a circular disk. The flattened area (and thus the pattern 28) has a diameter $\emptyset_D$ of about 12 mm. Alternatively, in another exemplary embodiment the diameter $\emptyset_D$ may have values which differ from 12 mm, in a range from about 9 mm to about 14 mm (in particular between about 10 mm and about 13 mm). The diameter $\emptyset_D$ of the flattened area having the pattern 28 corresponds to a typical diameter of an outer edge of a human iris.

In addition, the flattened area which forms the base area 20 of the eye model 10 is present as a circular disk. A diameter $\emptyset_G$ of the base area 20 is about 24 mm, at least in the exemplary embodiment shown in FIGS. 1B and 1C. Furthermore, the eye body 12 has a height $h_U$, extending perpendicularly with respect to the base area 20 of the eye model 10 in the area of the annular surface 18, of about 7.8 mm. A height $h_M$ of the eye body 12, extending perpendicularly with respect to the base area 20 in the area of the lateral surface 22, is about 2.2 mm.

In another exemplary embodiment, at least one of the values of the diameter $\emptyset_G$ and of the heights $h_U$, $h_M$ of the eye body 12 may differ from the stated values. Thus, in the case of the simulation of a smaller or larger portion of the human sclera, it may be provided that the diameter $\emptyset_G$ and the height $h_U$ vary as a function of one another.

As is clear in FIG. 1D, in the region of the flattened area the eye body 12 is provided with a recess 30 on the side of the annular surface 18 opposite from the pattern 28. Specifically, the recess 30 is a threaded hole which is introduced into the base area 20 of the eye model 10. The threaded hole 30 may be used, for example, to arrange (to screw, for example) the eye model 10 to a positioning device (not shown).

In the exemplary embodiment shown in FIG. 1D, the threaded hole 30 extends into the eye body 12, starting from an area in the middle of the base area 20 of the eye model 10. The threaded hole 30 also has a height $h_A$, extending perpendicularly with respect to the base area 20, of about 6.5 mm. In another exemplary embodiment, it may be provided that a plurality of recesses (for example, a plurality of threaded holes 30) is provided within the eye body 12. In addition, the recess or recesses may have an extension that is different from the extension as described with regard to the exemplary embodiment shown in FIG. 1D.

Figure 2A:
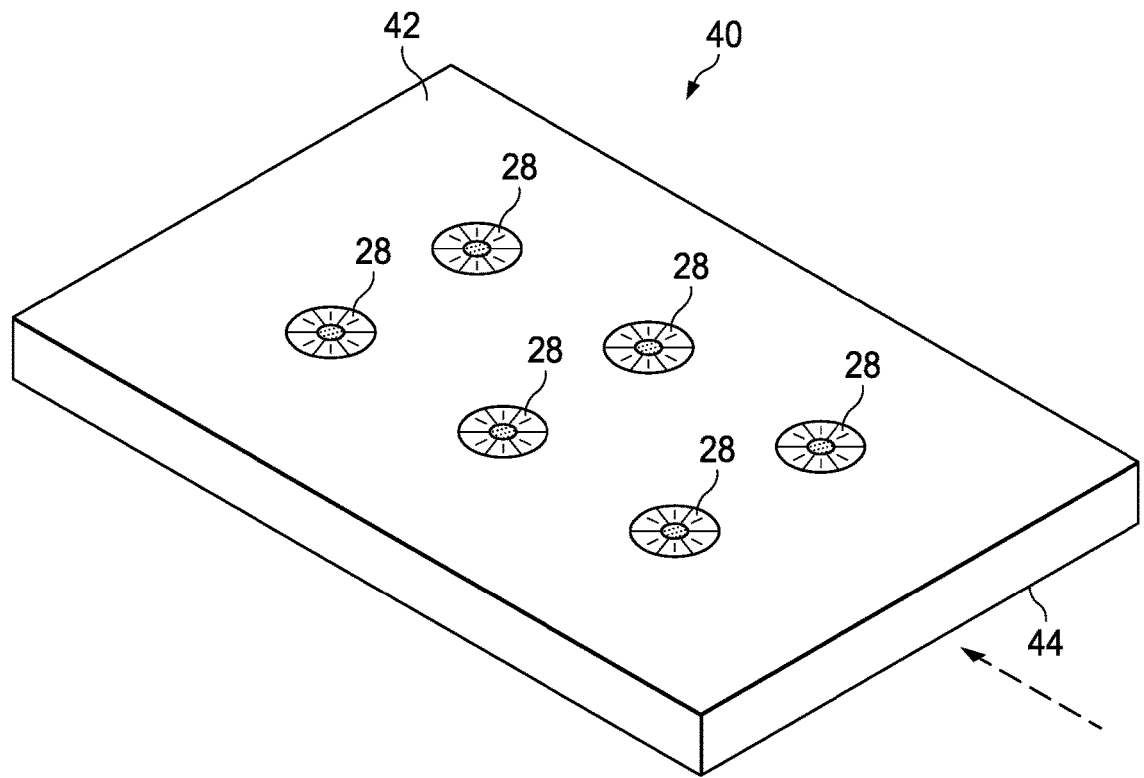
FIGS. 2A and 2B show one exemplary embodiment of a blank for producing the eye model.
Figure 2B:
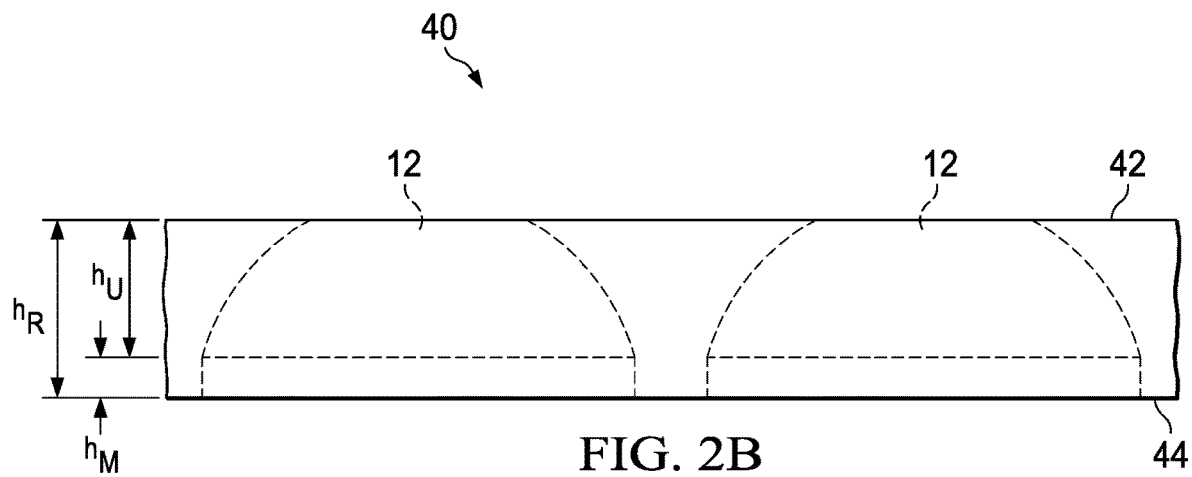

FIGS. 2A and 2B show schematic illustrations of one exemplary embodiment of a blank, denoted in general by reference numeral 40, made of the plastic material that is used for producing the eye body 12 (as described with reference to the preceding figures). FIG. 2A shows a perspective view, and FIG. 2B shows a side view, of the blank 40 (oriented in the direction of the arrow shown in dashed lines in FIG. 2A).

The plate-shaped blank 40 of the plastic material (in this case, white polyvinyl chloride) has two planar, oppositely situated blank flat sides 42, 44. A plurality of patterns 28 (see FIGS. 1A and 1B) is applied to a first of the blank flat sides 42 (a blank top side 42).

For producing the eye model 10 shown in the preceding figures, an eye body 12 or a plurality of eye bodies 12 is separated from the blank 40 (as marked by dashed lines in FIG. 2B). In the process, a side surface which joins the flattened areas of the eye body 12 is respectively produced in the blank 40. The cover surface 14 and the base area 20 of the eye model 10 are formed by the separated sections of the blank flat sides 42, 44. In the exemplary embodiment shown in FIG. 2B, a height $h_R$ which extends between the blank flat sides 42, 44 thus corresponds to a height of the eye model 10 which extends between the flattened areas of the eye body 12 (see FIG. 1C).

The plurality of the eye bodies 12 separated from the blank 40, i.e., the plurality of produced eye models 10, preferably corresponds to the plurality of the patterns 28 applied to (i.e., formed on) the blank 40. According to the exemplary embodiment of the blank 40 shown in FIG. 2A, the patterns 28 are already applied to the blank top side 42 before the eye body 12 is separated. For separating the eye body 12, the convexly curved peripheral surface 18 which surrounds the pattern 28 in a ring-like manner is produced in the blank 40. In addition, in the exemplary embodiment shown in FIG. 2B, the lateral surface 22 which adjoins the peripheral surface 18 is produced in the blank 40.

Applying the patterns 28 prior to the separation step simplifies and speeds up the production of the eye models 10 compared to individually applying a pattern 28 to a respective eye body 12 which has already been separated. In another exemplary embodiment, it may still be provided to apply an individual pattern 28 or a plurality of patterns 28 (on a planar and/or a convexly curved area of the surface) after the eye body 12 or the plurality of eye bodies 12 has been separated. The plurality of patterns 28 may substantially resemble each other. At least in this case, the applying of the plurality of patterns 28 to the eye bodies 12 or to the blank 40 may be carried out on an automated basis.

The pattern 28 is preferably imprinted on the blank 40 or the eye body 12 which has already been separated from the blank 40. Alternatively, the pattern 28 may be formed in some other way on the blank 40 or the eye body 12 which has already been separated from the blank 40. Thus, for example, it may be provided to paint on the pattern 28, or to apply an adhesive element which bears the pattern 28. It may be further provided to apply another pattern, such as a simulation of blood vessels, to the portion of the eye body 12 having the sclera simulation (as described with regard to FIGS. 1A to 1D).

In another exemplary embodiment, it may also be provided that only a single eye body 12 is separated from the blank 40 in order to produce a single eye model 10. At least in this case, the blank 40 may also be rectangular shaped, for example.

It is provided to mill out the eye bodies 12 from the blank 40 shown in FIGS. 2A and 2B. Alternatively or additionally, the separation of the eye bodies 12 (or of a single eye body 12) may include some other cutting or chipping machining of the blank 40. It is also provided that the eye bodies 12 are separated from the blank 40 in chronological succession.

However, the plurality of eye bodies 12 may also be separated partially simultaneously (for example, simultaneously in pairs) or simultaneously.

The production of the eye model 10 may include further steps. Thus, it is provided to introduce the threaded hole 30 shown in FIG. 1D (or a plurality of threaded holes 30) into the blank 40 in association with each eye body 12 to be separated from the blank 40. Specifically, the threaded hole 30 is introduced into the blank 40 (for example, by milling out plastic material), starting from the second blank flat side 44 situated opposite from the blank top side 42. Alternatively, the threaded hole 30 may also be introduced into the eye body 12 after the eye body 12 is separated, starting from the base area 20 of the eye body.

In an alternative embodiment, at least some of the steps of producing the eye model 10 may be replaced by 3D printing. For example, the eye body 12 may be 3D printed with the plastic material (such as white polyvinyl chloride). In this case, the 3D printing may further include the step of applying the pattern 28 to the eye body 12 by printing colored plastic material (such as colored polyvinyl chloride).

Figure 3:
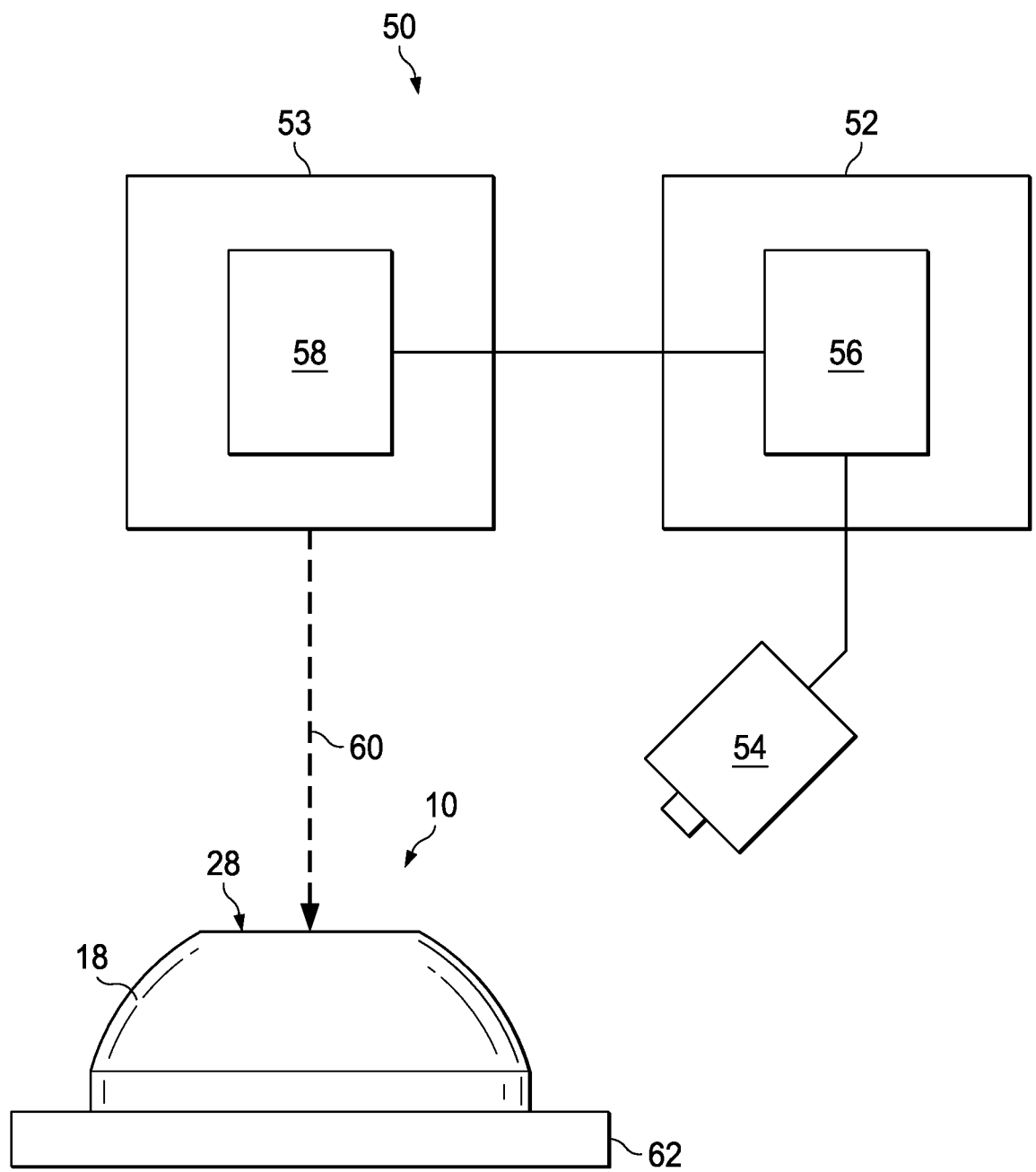
FIG. 3 shows a device for using the eye model.

FIG. 3 shows, in a highly schematic block diagram, one exemplary embodiment of a device, denoted in general by reference numeral 50, for using the eye model 10 described with reference to FIGS. 1A to 2B.

The device 50 includes an eye tracking system 52 and a laser device 53 for refractive laser treatment of a human eye. The eye tracking system 52 may be an eye tracker which is designed for detecting and quantifying a translational and a rotational eye movement in multiple dimensions, in particular in more than two dimensions. The eye tracker 52 may, for example, be part of the laser device 53, illustrated in a highly schematic manner.

The eye tracker 52 may be implemented in various ways known to those skilled in the art. In the exemplary embodiment shown in FIG. 3, the eye tracker 52 includes an infrared camera unit 54 and a processing unit 56. The eye tracker 52 further includes means (not shown here) for obtaining information related to the direction along the optical axis of the human eye or the eye model 10, such as information on a movement of the eye or the eye model 10 along the optical axis. The means may, for example, include a stripe projector located in the field of view of the infrared camera unit 54.

The infrared camera unit 54 is configured for recording a plurality of infrared images of the eye model 10 (and the stripe projector), for example by means of one or a plurality of infrared cameras positioned around the eye model 10. It is provided that such an infrared image of the eye model 10 contains the pattern 28 and at least one portion of the sclera simulation which adjoins the pattern 28 (i.e., an area of the annular surface 18 of the eye body 12). On account of the plastic material described with reference to FIGS. 1A to 2B, the sclera simulation appears bright, even under infrared illumination by the infrared camera unit 54. Thus, the pattern 28 contrasts in color with the bright sclera simulation, even under infrared illumination, i.e., in the infrared image.

The processing unit 56 is configured for determining a position of the center of the simulation of the eye pupil 30 and an orientation of the simulation of the iris structure 32 (see FIGS. 1A, 1B, and 2A) relative to the eye tracker 52 from a single infrared image and a plurality of infrared images of the eye model 10. Depending on the design of the pattern 28, in another exemplary embodiment it may be provided, for example, that the processing unit 56 determines only the position of the center of the simulation of the eye pupil 30, for example by recognizing the pupil margin.

In the exemplary embodiment shown in FIG. 3, the eye tracker 52 or the processing unit 56 is connected to a control system 58 of the laser device 53 via a suitable interface, so that the data concerning the movement of the eye model 10 collected by the eye tracker 52 may be relayed to the control system 58 in order to carry out the control of laser radiation generated by the laser device 53, taking into account the eye position and eye orientation determined by the eye tracker 53. The beam path of the laser radiation is indicated by the arrow denoted by reference numeral 60.

In the exemplary embodiment shown in FIG. 3, the device 50 also includes a positioning device 62 on which the eye model 10 is arranged. The eye model 10 may thus be fixed, for example, by screwing the eye model 10 onto threaded sections (screws, for example), not shown, of the positioning device 62. It is provided to situate the positioning device 62, together with the eye model 10 arranged thereon, in the area of a head support of a patient table (not illustrated here), for example by inserting into the patient table by means of a simple form-locked fit.

The positioning device 62 is also designed to mechanically adjust the position and orientation of the eye model 10. A relative movement between the eye model 10 and the eye tracker 52 is thus effected. Alternatively or additionally, in another exemplary embodiment the relative movement between the eye tracker 52 and the eye model 10 may take place by changing the position and orientation of the eye tracker 52.

As the result of such a relative movement between the eye model 10 and the eye tracker 52, the three-dimensional sclera simulation (as described with reference to FIGS. 1A to 2B) allows the simulation of a translational movement of a human eye along and perpendicular to the optical axis, and also of a rotational movement of the eye about the optical axis (eye roll about the z-axis) and the spatial axes perpendicular thereto (eye roll about the x-axis and the y-axis). The effected relative movement may be detected and quantified during the movement by repeated infrared image recording and infrared image processing by means of the eye tracker 52. Thus, the functionality of the eye tracker 52 may be tested, for example calibrated, for all degrees of freedom of eye movements (as they occur, for example, during a refractive laser treatment).

When the eye model 10 is used in conjunction with the device shown in FIG. 3, based on simulated movements of the eye model 10, such as effected by the positioning device 62, one or more function tests of the laser device 53 may also be carried out, and/or the laser device 53 may be calibrated, and/or a laser treatment of a human eye by means of the laser device 53 with simultaneous eye tracking may be simulated.

The invention claimed is:

1. A test device for testing functionality of and calibrating an eye tracker configured for use with a laser device for refractive eye surgery, using an eye model, comprising:
   an eye model comprising:
      a flattened area forming a cover surface of the eye model;
      a sclera simulation which is made of a bright plastic material, the plastic material containing a polyvinyl chloride at least as the main component, the sclera simulation forming an annular surface in accordance with the shape of a spherical or ellipsoidal surface, the sclera simulation surrounding the flattened area;
      a pattern which contrasts in color with the sclera simulation, the pattern simulating an eye pupil and an iris structure wherein the pattern is situated on the flattened area;

wherein the material of the sclera simulation is configured to appear white and the pattern is configured to contrast in color with the sclera simulation under infrared illumination; and a flattened base area on the side of the annular surface opposite from the pattern, the region of the flattened base area provided with a threaded hole;

a positioning device configured to mechanically adjust the position and orientation of the eye model, the threaded hole used to arrange the eye model to the positioning device, wherein the eye model is movable by the positioning device to different positions and orientations;

an eye tracker configured to detect and quantify the movement of the eye model as it is moved by the positioning device;

wherein the eye tracker further comprises:

an infrared camera configured to record infra-red images of the eye model as it is moved by the positioning device, wherein the images contain the pattern and at least one portion of the sclera simulation which adjoins the pattern; and a processing unit which is configured for determining a position and/or an orientation of the pattern within recorded infrared images.

2. The device of claim 1, wherein the plastic material is white in the area of the sclera simulation.

3. The device of claim 1, wherein the transition from the annular surface to the flattened area is formed by a ring-shaped edge.

4. The device of one of claim 1, wherein the pattern is formed by imprinting or painting of the eye body, or by adhering to the eye body an adhesive element which bears the pattern.

5. The device according to one of claim 1, wherein the surface of the eye body in the area of the sclera simulation forms a convexly curved annular surface.

6. The device according to claim 1 wherein the eye model is situated on a patient table in the area of a head support of the patient table while the images are recorded.

7. The device of claim 1 wherein the processing unit is further configured to determine a position of a center of the eye pupil and/or an orientation of the simulation of the iris structure within the recorded infrared images to calibrate the eye tracker.

8. The device of claim 1 wherein the positioning device is further configured to adjust the position and orientation of the eye model to simulate translational eye movement along an axis perpendicular to an optical axis and rotational eye movement about the optical axis.

* * * * *